United States Patent [19]
Carn et al.

[11] Patent Number: 5,425,702
[45] Date of Patent: Jun. 20, 1995

[54] SOFT TISSUE SUPPORT FOR HIP AND SHOULDER

[75] Inventors: Ronald M. Carn, Redding, Calif.; Angela E. Gonzales, Albuquerque, N. Mex.

[73] Assignee: SunMed, Inc., Redding, Calif.

[21] Appl. No.: 17,335

[22] Filed: Feb. 11, 1993

Related U.S. Application Data

[63] Continuation of Ser. No. 612,253, Nov. 9, 1990, abandoned, which is a continuation-in-part of Ser. No. 440,857, Nov. 20, 1989, abandoned.

[51] Int. Cl.$^6$ .............................................. A61F 5/04
[52] U.S. Cl. ........................................ 602/62; 602/1; 602/57; 602/60; 602/61; 602/75; 602/76; 604/388
[58] Field of Search .................. 128/99.1, 100.1, 101.1; 602/1, 57, 60, 61, 62, 64, 65, 66, 75, 76, 77; 604/388

[56] References Cited

U.S. PATENT DOCUMENTS

| | | | |
|---|---|---|---|
| 819,975 | 5/1906 | Bracco, Sr. | |
| 1,727,897 | 9/1929 | Meyers et al. | 602/62 |
| 1,916,298 | 7/1933 | Brohman | 128/96 |
| 2,310,864 | 2/1943 | Pegg | 128/155 |
| 2,354,697 | 8/1944 | Muller | 2/27 |
| 2,461,208 | 2/1949 | Goforth | 128/96 |
| 2,520,063 | 8/1950 | Rishcoff | 2/36 |
| 2,586,355 | 2/1952 | Leven | 2/41 |
| 2,606,551 | 8/1952 | Piper | 128/96 |
| 2,778,358 | 1/1957 | Keles | 128/78 |
| 2,787,266 | 4/1957 | Scholl | 602/77 |
| 2,802,465 | 8/1957 | Brown | 128/159 |
| 3,046,981 | 1/1962 | Biggs, Jr. et al. | 128/80 |
| 3,086,529 | 4/1963 | Munz et al. | 128/327 |
| 3,091,238 | 5/1963 | De Bogory, Sr. | 128/95 |
| 3,097,641 | 7/1963 | Nelkin | 128/96 |
| 3,130,730 | 4/1964 | Zanca | 128/524 |
| 3,130,731 | 4/1964 | Zdan | 128/531 |
| 3,194,233 | 7/1965 | Peckham | 128/80 |
| 3,194,234 | 7/1965 | Ducknan et al. | 128/95 |
| 3,280,819 | 10/1966 | Weeks | 128/525 |
| 3,308,813 | 3/1967 | Loeffel | 128/96 |
| 3,452,748 | 7/1969 | Caprio | 128/78 |
| 3,474,780 | 10/1969 | Fuchs | 128/95 |
| 3,512,776 | 5/1970 | Thomas, Sr. | 128/165 |
| 3,524,449 | 8/1970 | Peters | 128/524 |
| 3,526,221 | 9/1970 | Garber | 128/95 |
| 3,623,488 | 11/1971 | Nakayama | 128/549 |
| 3,783,879 | 1/1974 | Stalder | 128/570 |
| 3,856,004 | 12/1974 | Cox | 128/87 |
| 3,888,244 | 6/1975 | Lebold | 128/165 X |
| 3,926,186 | 12/1975 | Nirschl | 128/165 |
| 4,047,250 | 9/1977 | Norman | 128/165 X |
| 4,067,330 | 1/1978 | Roache | 128/149 |
| 4,133,311 | 1/1979 | Karczewski | 128/166 |
| 4,182,318 | 1/1980 | Beige et al. | 128/165 X |
| 4,182,338 | 1/1980 | Stanulis | 128/325 |
| 4,231,358 | 11/1980 | Atchison | 128/171 X |
| 4,351,324 | 9/1982 | Walker | 128/96 |
| 4,370,977 | 2/1983 | Mauldin et al. | 128/80 |
| 4,370,978 | 2/1983 | Palumbo | 128/80 |
| 4,497,315 | 2/1985 | Fettweis et al. | 128/78 |
| 4,497,316 | 2/1985 | Lilla | 128/94 |
| 4,550,724 | 11/1985 | Berrehail | 128/165 X |
| 4,574,790 | 3/1986 | Wellershaus | 128/78 |
| 4,644,939 | 2/1987 | Coleman | 128/78 |
| 4,644,946 | 2/1987 | Cremona-Bonato | 128/165 |

(List continued on next page.)

OTHER PUBLICATIONS

Elasto-Gel "Shoulder Therapy Wrap" by Southwest Technologies, Inc., Kansas, City, Mo.
"Redi-Grip Hip Spica Support" by Biomet, Inc., Warsaw, Indiana.

*Primary Examiner*—Randall L. Green
*Assistant Examiner*—P. Zuttarelli
*Attorney, Agent, or Firm*—Kelly, Bauersfeld & Lowry

[57] ABSTRACT

A soft tissue support is disclosed. The apparatus preferably comprises a two-ply garment adapted to provide support for hip and shoulder wounds. The garment itself comprises a suspension portion and a tissue support wrap portion adapted to encircle the traumatized parts, and further provides support for the buttocks and the deltoid.

29 Claims, 4 Drawing Sheets

U.S. PATENT DOCUMENTS

| | | | |
|---|---|---|---|
| 4,702,234 | 10/1987 | Huntjens | 128/77 |
| 4,709,692 | 12/1987 | Kirschenberg | 128/78 |
| 4,724,831 | 2/1988 | Huntjens | 128/80 |
| 4,765,318 | 8/1988 | Tranberg et al. | 128/80 |
| 4,769,854 | 9/1988 | Williams | 2/22 |
| 4,785,803 | 11/1988 | Benckhuijsen | 128/87 |
| 4,829,994 | 5/1989 | Kurth | 128/96.1 |
| 4,878,490 | 11/1989 | Scott | 128/165 X |
| 4,884,563 | 5/1990 | Sessions | 128/155 |
| 4,926,848 | 5/1990 | Shimkus | 128/169 |
| 4,926,850 | 5/1990 | Lott et al. | 128/155 |
| 4,926,851 | 5/1990 | Bulley | 128/157 |
| 4,932,079 | 6/1990 | Bridgenater | 2/313 |
| 4,977,893 | 12/1990 | Hunt | 128/165 |
| 5,107,827 | 4/1992 | Boyd | 602/76 |
| 5,181,906 | 1/1993 | Bauerfeind | 602/61 |
| 5,195,950 | 3/1993 | Delannoy | 602/77 |

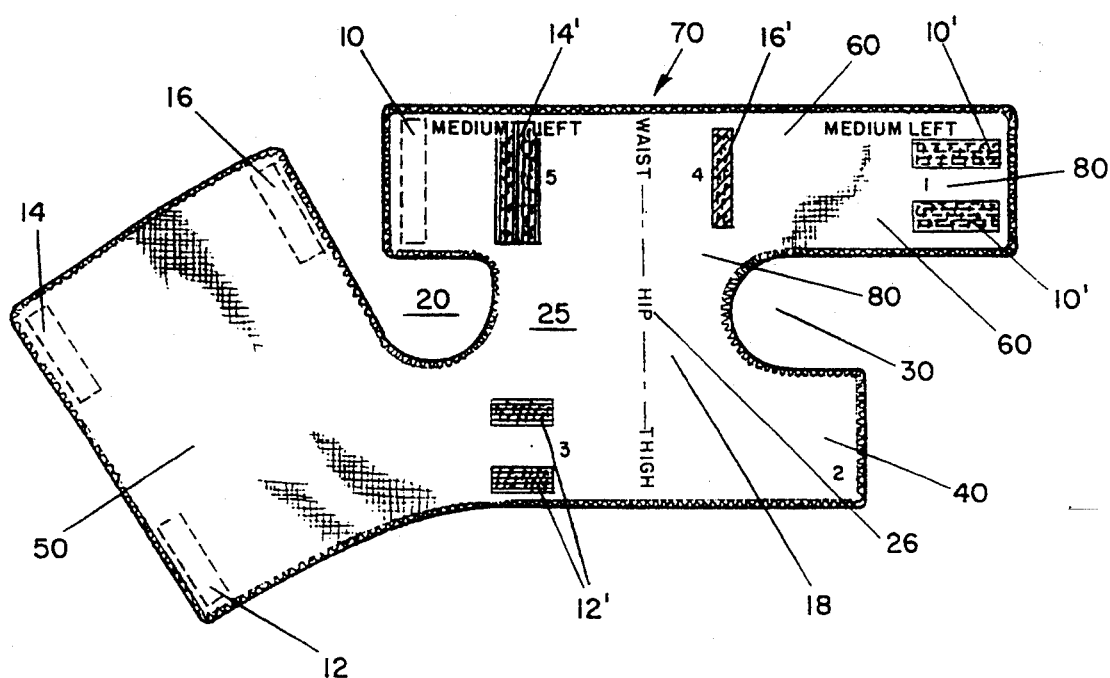
FIG—1
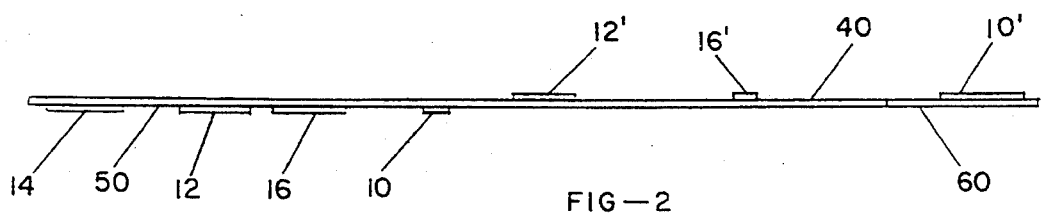
FIG—2
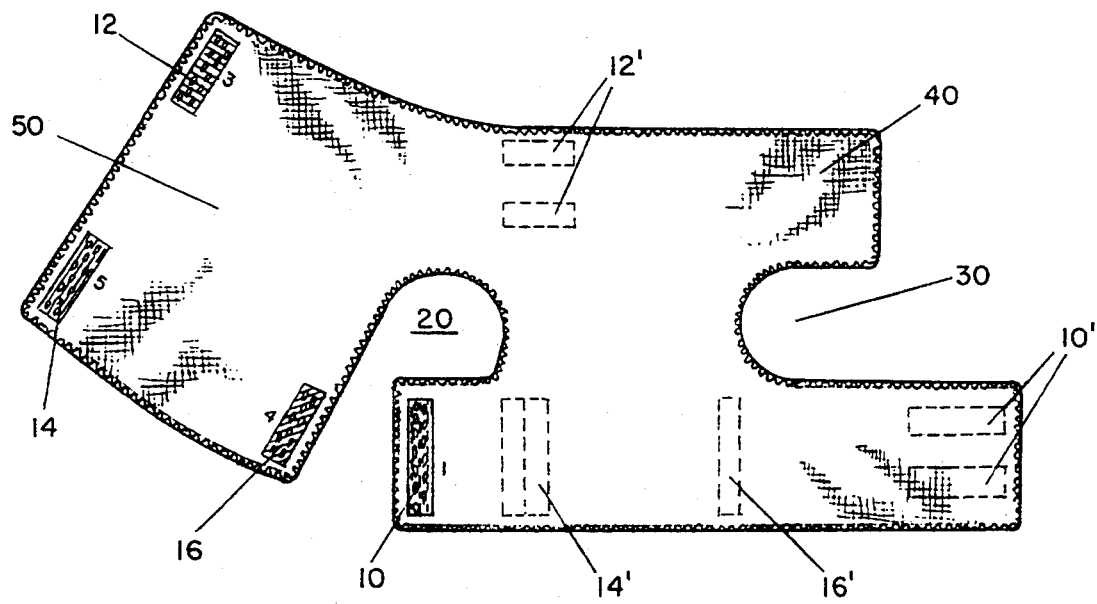
FIG—3

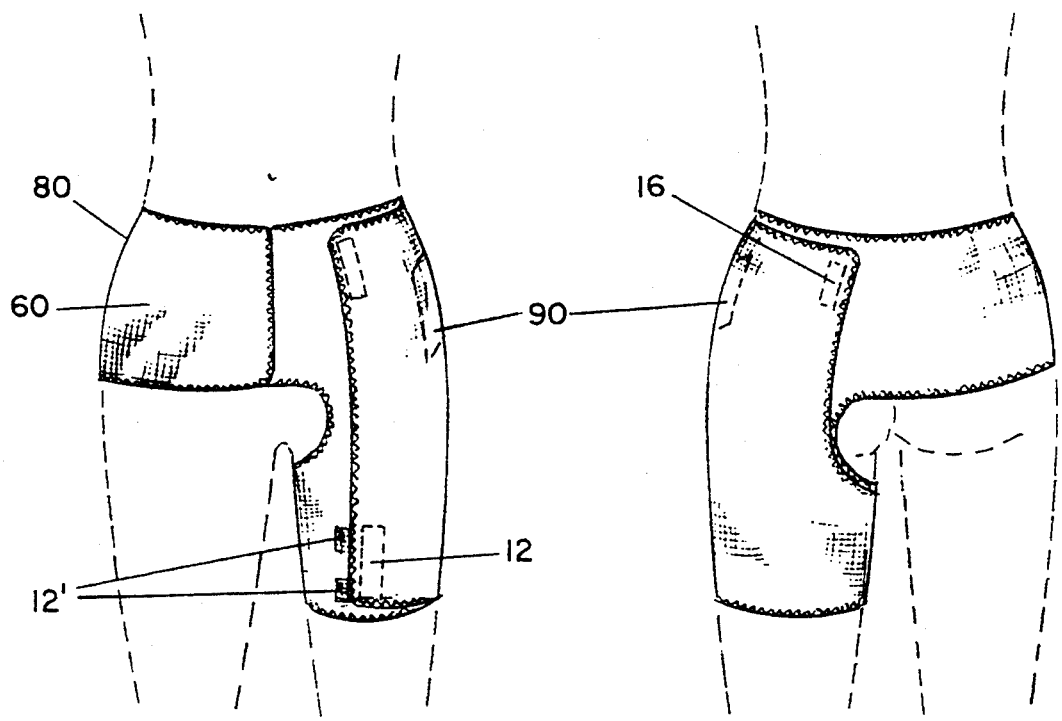
FIG—4  FIG—5
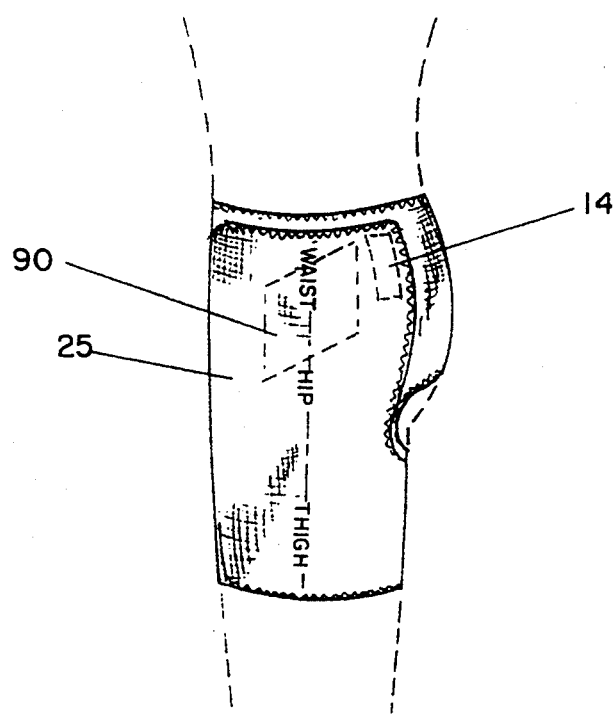
FIG—6

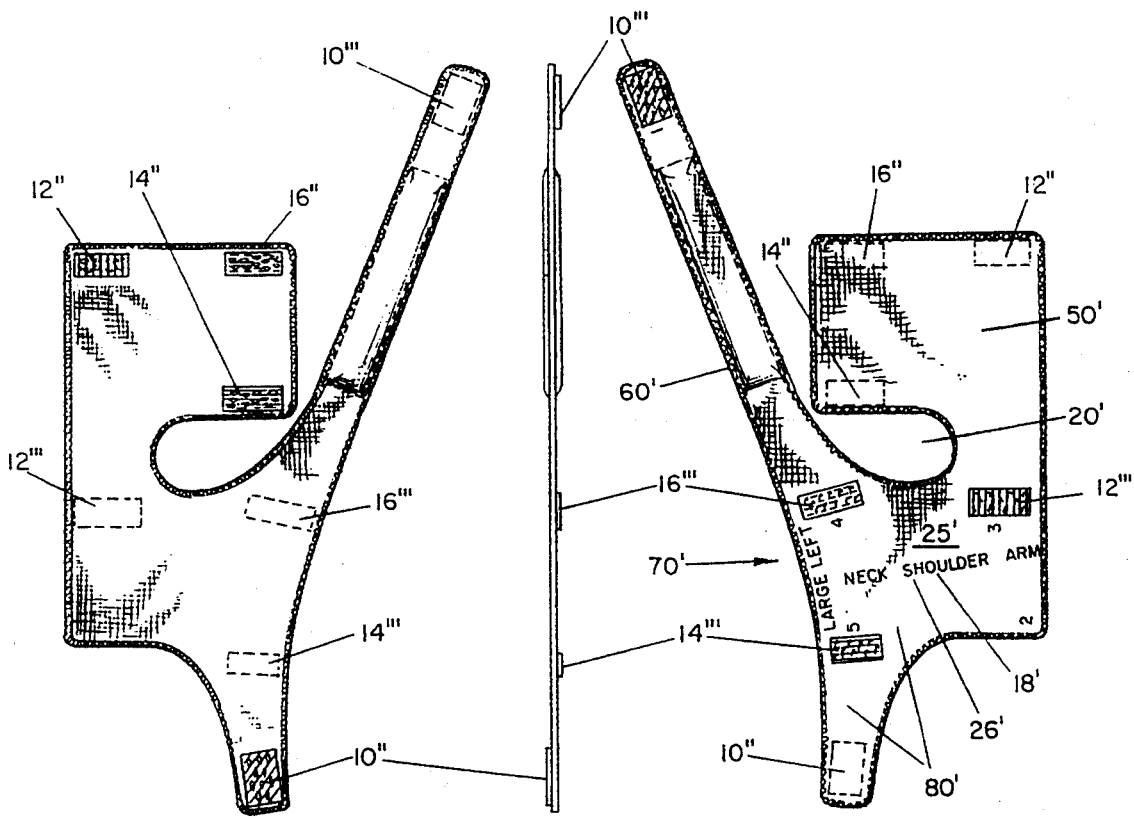

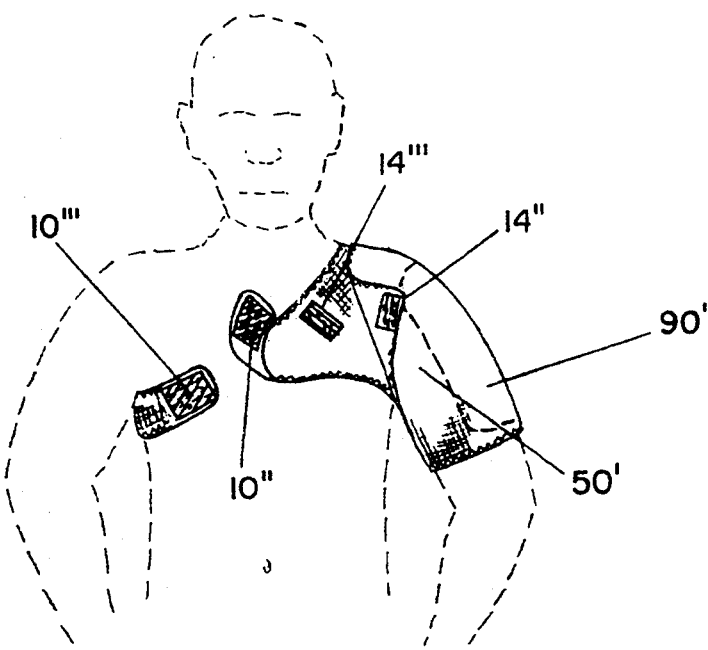
FIG—12
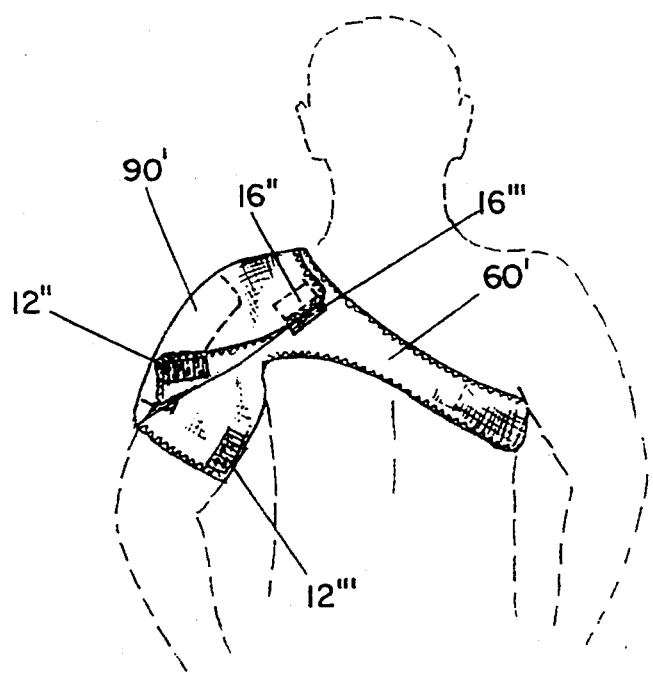
FIG—13

SOFT TISSUE SUPPORT FOR HIP AND SHOULDER

CROSS-REFERENCE TO RELATED APPLICATIONS

This application is a continuation application of U.S. patent application Ser. No. 07/612,253 filed Nov. 9, 1990; now abandoned; which was a continuation-in-part application of U.S. patent application Ser. No. 07/440,857 filed Nov. 20, 1989; now abandoned.

BACKGROUND OF THE INVENTION

1. Field of the Invention (Technical Field)

The invention relates to the field of medical sciences and in particular to apparatuses which facilitate proper wound healing after hip and shoulder surgeries.

2. Background Art

The care of post-operative hip and shoulder wounds is of paramount importance. Compromised healing can result in infection, swelling, pain, disability, and even death.

For optimum post-operative hip and shoulder wound healing, the following conditions must exist:

The incision and the area surrounding it must be clean and free from bacteria;

Even pressure must be maintained over the surgical incision, thus, minimizing potential post-operative bleeding;

The soft tissue surrounding the incision must be supported in order to enhance healing by minimizing swelling and reducing pressure along the incision line; and The neurological and circulatory integrity of the affected joint must be maintained.

The typical prior methods for managing post-operative hip and shoulder wounds include adhesive tapes. Some of these tapes have built in elasticity intended to provide compression and support over the wound. The disadvantages of these adhesive tapes are:

Pressure over the surgical incision is inconsistent and uneven;

Soft tissue surrounding the wound is not supported; and

When the tape is removed, the skin beneath it can blister causing unnecessary pain to the patient as well as a potential site for infection.

Other hip and shoulder wound management methodologies include elastic and cotton roll dressings. These are applied in a circular fashion around the waist or chest and the affected extremity.

These methods have the following disadvantages:

Usually more than one roll must be applied on the affected extremity. This makes them difficult to apply and often requires two people; and They frequently become disheveled and bunched causing insufficient pressure over the surgical wound and inadequate support to the soft tissue surrounding the wound.

The method of applying roll dressings is dependent on the technique of the individual(s) applying the dressings. In the post-operative period, many different people may remove and reapply a patient's rolled dressing. This results in inconsistent pressure over the surgical wound and variable support to the soft tissue surrounding the incision;

The surgical dressing can become dislodged causing a potential for infection; and When disheveled the rolls can become constrictive in the axilla and groin areas placing undo pressure on neurovascular structures. This impairs circulation and may cause thrombophlebitis and/or irreversible nerve damage.

BIOMET (trademark) manufactured by Biomet, Inc., Airport International Park, Warsaw, Ind. (effective date of brochure unknown) provides a post-operative hip support or "hip spica," but lacks individualized fit and indexed application. U.S. Pat. No. 4,644,939, to Coleman, entitled Shoulder Brace, discloses a shoulder brace applicable for dislocations, not shoulder wounds. U.S. Pat. No. 4,785,803, to Benckhuijsen, entitled Shoulder Truss, likewise is designed for shoulder support to counteract cervical syndrome; it is not designed to support wound tissue. U.S. Pat. No. 3,046,981, to Biggs, Jr., et al, entitled Knee Brace, teaches a multi-strapped knee brace inapposite to the present invention. U.S. Pat. No. 4,724,831, to Huntjens, entitled Knee Support for Aiding Proprioceptive Innervation, likewise teaches a knee brace for supporting knee ligaments, as opposed to wound dressing and tissue support. U.S. Pat. No. 3,194,234, to Duckman, et al, entitled Postoperative Binder, teaches a postoperative binder for abdominal wounds. U.S. Pat. No. 4,574,790, to Wellershaus, entitled Orthopedic Device for Treating Hip Dysplasia and Hip Dislocation, teaches a complex hip brace inapplicable for post-operative use. U.S. Pat. No. 4,497,315, to Fettweis, et al., entitled Orthopedic Device for Treating Hip Displeasure and Hip Luxation, likewise is not concerned with soft tissue support; neither is U.S. Pat. No. 2,778,358, to Keles, entitled Orthopedic Spinal and Hip Joint Attachment.

U.S. Pat. No. 3,474,780, to Fuchs, entitled Aid for Alleviating Varicose Veins, is a device for applying pressure to pelvic varicose veins. U.S. Pat. No. 4,829,994, to Kurth, entitled Femoral Compression Device for Post-Catheterization Hemostasis, provides pressure over the femoral artery, but is unconcerned with hip or shoulder wound support. U.S. Pat. No. 4,709,692, to Kirschenberg, et al., entitled Thigh Mounted Lower Back Support Belt, provides orthopedic spinal support and is likewise unconcerned with soft tissue wound support. Similarly, U.S. Pat. No. 2,802,465, to Brown, entitled Supporting Undergarment, also intended for spinal and pelvic support. U.S. Pat. No. 3,280,819, to Weeks, entitled Foundation Garment, has no relation to soft tissue wound support.

U.S. Pat. No. 4,769,854, to Williams, entitled Kicking Spat, provides a leather foot attachment as a football kicking aid. U.S. Pat. No. 4,133,311, to Karczewski, entitled Ankle Support Structure, provides ankle support, but is unconcerned with soft tissue wound support. The Elastic-Gel Shoulder Therapy Wrap, by Southwest Technologies, Inc., provides moist heat therapy for shoulder muscles.

SUMMARY OF THE INVENTION (DISCLOSURE OF THE INVENTION)

The present invention relates to a soft tissue support garment comprising a suspension portion and a tissue support wrap portion suspended from the tissue support portion. The suspension portion preferably comprises first indices corresponding to anatomic parts, and second indices on the suspension portion and the tissue support wrap portion corresponding to securement areas.

The invention further comprises a soft tissue support garment wherein the suspension portion and the tissue support wrap portion comprise elastic fabric which may further comprise one-ply or two-ply elastic fabric. Further, the two-ply elastic fabric may comprise two plies in angularly overlapping relationships and may further comprise two plies in orthogonally overlapping relationship.

The present invention further comprises a soft tissue support garment wherein the first indices comprise symbols corresponding to anatomic parts, and such symbols may further comprise printed matter. The soft tissue support garment may further comprise second indices comprising symbols corresponding to securement areas, and such symbols may further comprise color coding, numbers, and numbers and color coding.

The invention further comprises a soft tissue support garment comprising first indices corresponding to waist, hip, and thigh parts, and neck, shoulder, and arm parts. Further, the invention comprises a suspension portion which may encircle the waist or the upper torso.

The invention further comprises a soft tissue support garment comprising a suspension portion adapted to encircle a first anatomic part, and a tissue support wrap portion suspended from the suspension portion and adapted to encircle a second anatomic part. The invention first comprises first indices on the suspension portion corresponding to the first and second anatomic parts, and second indices on the suspension portion and tissue support wrap portion corresponding to securement areas.

The invention further comprises a soft tissue support garment wherein the suspension portion comprises a cincture portion and a pendent portion. The cincture portion may further encircle the waist or the upper torso. The tissue support wrap portion may encircle the thigh or the upper arm and shoulder.

The invention further comprises a method of using a soft tissue support garment comprising the steps of providing a garment having a suspension portion and a tissue support wrap portion, indexing the garment to correspond with specific anatomic areas, indexing the garment to indicate specific securement areas, wrapping and securing the suspension portion of the garment, and subsequently wrapping and securing the tissue support wrap portions of the garment.

The method of using the soft tissue support garment may further comprise the additional steps of layering a fabric of elastic material, providing printed matter on the garment and coloring specific securement areas.

The method of using the soft tissue support garment may comprise the additional steps of matching and mating colored securement areas, wrapping a tongue portion under a specific anatomic part in one direction, wrapping the tissue support wrap portion about the specific anatomic part in an opposite direction, and matching and mating colored securement areas.

An object of the invention is the provision of even pressure over surgical wounds as well as gentle support of surrounding soft tissue.

A further object of the present invention is the stabilization of sterile dressings without adhesive tape or roll dressings.

Yet another object of the present invention is the minimization of pressure on groin or axilla while supporting hip and shoulder wounds.

An advantage of the present invention is that the unique shape is sized and not reversible, resulting in closer fits.

A further advantage of the present invention is the provision of labelling and indexing of the garment to assure correct application. Yet another advantage of the present invention is that the garment may be of one-piece two-ply elastic construction.

Still another advantage of the present invention is that the double wrap design provides a pouch for therapeutic aids, such as ice packs and heating elements.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention.

FIG. 1 is a side view of a preferred left side hip and thigh wrap garment embodiment;

FIG. 2 is a side view of the FIG. 1 embodiment;

FIG. 3 is a side view of the obverse side of the FIG. 1 embodiment;

FIG. 4 is a front view of the FIG. 1 hip and thigh garment wrap embodiment in position;

FIG. 5 is a rear view of the FIG. 1 hip and thigh garment embodiment in position;

FIG. 6 is a side view of the FIG. 1 hip and thigh garment embodiment in position;

FIG. 7 is a side view of a preferred left side shoulder and upper arm wrap garment embodiment;

FIG. 8 is a side view of the FIG. 7 embodiment;

FIG. 9 is a side view of the obverse side of the FIG. 7 embodiment;

FIG. 10 is a side view of the FIG. 7 embodiment;

FIG. 11 is a side view of the FIG. 7 embodiment;

FIG. 12 is a front view of the FIG. 7 shoulder and upper arm wrap garment embodiment in position; and FIG. 13 is a rear view of the FIG. 7 shoulder and upper arm wrap garment embodiment in position.

DESCRIPTION OF THE PREFERRED EMBODIMENTS (BEST MODES FOR CARRYING OUT THE INVENTION)

Reference is now made to FIGS. 1-6 which show the preferred or first embodiment of the invention. As seen therein, soft tissue garment 70 comprises suspension portion 80 comprising elongate cincture portion in this instance adapted to encircle the waist. Cincture portion 60 further comprises indices (e.g., printing, sticking, marking, or the like) laterally thereon indicating relative size and side of the body to which the garment is to be applied.

Garment 70 further comprises fastening, closure or securement areas 10, 10', 12, 12', 14, 14', 16, and 16'. In the preferred embodiment, fastening, closure, or securement areas 10, 10', 12, 12', 14, 14', 16, and 16' comprise hook and loop (VELCRO®) fasteners; alternatively closure or securement areas 10, 10', 12, 12', 14, 14', 16, and 16' may comprise snaps, zippers, ties, metallic hooks and fabric loops and other fasteners well known to those ordinarily skilled in the art.

Closure or securement areas 10, 10', 12, 12', 14, 14', 16, and are also numbered and color coded to facilitate ease of application. The patient or health care professional merely matches numerals, preferably in order, and colors of the closure areas to properly secure the cincture about the waist.

Suspension portion 80 further comprises pendent portion 25. Pendent portion 25 extends downwardly from cincture portion 60, and comprises a narrow neck portion 26 found by anterior and posterior crotch cutouts 20 and 30, respectively. Pendent portion 25 further comprises elongate tongue portion 40, and is attached to obliquely extending tissue support wrap portion 50. Pendent portion 25 and cincture portion 60 also comprise indices 18 relating specific garment areas to specific anatomical areas. Pendent portion 25 further comprise fastening or closure areas 12' which are also numbered and color coded.

Tissue support wrap portion 50 is supported by suspension portion and, when in position, extends downwardly and laterally over the waist and hip, while encircling the thigh. Tissue support wrap portion 50 provides soft tissue support for wounds, resulting from hip surgery, pelvic surgery, iliac bone grafts and the like. Tissue support wrap portion 50 directly overlies the sterile dressing covering the wound, providing gentle, uniform compressive support of the wound, and stabilizes the sterile surgical dressing. Tissue support wrap portion 50 likewise comprises securement or closure areas 12, 14, and 16.

Application of soft tissue support garment 70 initially requires correct size and body side selection. Left and right body sides are not interchangeable as they comprise mirror images of each other. Assuming correct size and body side selection, the garment is loosely positioned about the appropriate waist, hip and thigh area with garment indices matching anatomical parts in a straight line bisecting the exterior portion of the leg from waist to thigh. Cincture portion 60 is then drawn about the waist and secured anteriorly by mating matching closure areas 10 and 10'. Thereafter, tongue portion 40 is passed through the crotch from posterior to anterior. Tissue support wrap portion 50 is then passed through the crotch from anterior to posterior, over tongue portion 40. Tissue support wrap portion 50 is brought forward again laterally and anteriorly of the hip and thigh, over the dressed wound. Tissue support wrap portion 50 is then secured in position by mating and matching closure or securement means 14, 14', 16, 16' and likewise numbered (see small numerals 1-5) and color coded.

It should be noted that looping tissue support wrap portion 50 over tongue portion 40 may provide a large pocket or pouch 90 over the hip which comprises a receptacle for therapeutic aids, such as ice packs, heating devices, and the like. Additional pockets or pouches may also be provided.

Reference is now made to FIGS. 7–13, which depict an alternative or second embodiment of the invention. Garment 70' is adapted to provide soft tissue protection for upper arm and shoulder wounds.

Garment 70' also comprises a suspension portion 80' comprising a cincture portion 60' and a pendent portion 25', as well as a tissue support wrap portion 50'. Cincture portion 60' is elongate and adapted to encircle the upper torso. Cincture portion 60' and pendent portion 25' also comprise indices (e.g., printing, stitching, marking, or the like) laterally thereon indicating relative size and side of the body to which the garment is to be applied.

Garment 70' further comprises closure or securement areas 10'', 10''', 12'', 12''', 14'', 14''', 16'', and 16'''. Again, as in the first preferred embodiment, closure areas 10'', 10''', 12'', 12''', 14'', 14''', 16'', and 16''' may comprise hook and loop fasteners numbered and color coded to facilitate attachment of the garment. Alternatively, other fasteners may be used, including snaps, ties, zippers and the like.

Suspension portion 80' further comprises pendent portion Pendent portion 25' also extends downwardly from cincture portion and comprises a narrow neck portion 26' formed by axilla cutout Similarly, pendent portion 25' comprises a reduced tongue portion, and is likewise obliquely attached to tissue support wrap portion 50'. Pendent portion 25' and cincture portion 60' also comprise indices specifically relating garment areas to specific body parts. Pendent portion 25' further comprises fastening or securement areas 12''', 14''', and 16''', which are numbered and color coded to facilitate garment application.

Tissue support wrap portion 50' is supported by suspension portion 80', and when in position, extends downwardly and laterally about the shoulder and upper arm. As in the first embodiment of the invention, tissue support wrap portion 50' provides support for wounds such as resulting from shoulder surgery, bursitis, fractures and the like.

Application of garment 70' parallels that of garment 70. Assuming correct size and body side (again, right and left sides are not interchangeable), garment 70' is loosely positioned about the upper torso with garment indices vertically matching body parts in a straight line bisecting the shoulder and arm from the neck to the upper arm. Cincture portion 60' is drawn about the upper torso and drawn under the opposing arm. As before, tongue portion is extended, anterior to posterior, under the affected shoulder along the axilla. Tissue support wrap portion 50' is extended, posterior to anterior, over tongue portion, and the axilla, wrapped about the shoulder and upper arm, and secured by mating numbered (see small numerals 1-5), color coded closure areas 10'', 10'''; 12'', 12'''; 14'', 14'''; and 16'', 16'''.

Also, as before, looping tissue support wrap portion 50' over tongue portion creates a large sac or pouch 90' adapted for therapeutic uses, such as ice packs, heat elements, medication, and the like.

Both garments are preferably made of a cotton-LYCRA® blend which provides elasticity as well as durability. Preferably, the garment is layered of two-ply construction orthogonally related. This construction provides four-way elasticity; alternatively, the plies may be oriented relative to each other at other than right angles. Alternatively, a single-ply structure may be provided.

Further, the thickness and elasticity of fabric may be varied to accommodate different patients and conditions. For example, by adjustment of fabric thickness, if necessary, both left and right side garments may be worn simultaneously. Further, additional pads or padding may be provided to the garment to prevent abrasion.

Although the invention has been described with reference to these preferred embodiments, other embodiments can achieve the same results. Variations and modifications of the present invention will be obvious to those skilled in the art, and it is intended to cover in the appended claims all such modifications and equivalents.

What is claimed is:

1. A soft tissue wound support garment comprising:
   cincture means configured to encircle a first anatomic part;
   pendent means suspended from said cincture means;
   tissue support wrap means suspended sidelong from said pendent means and configured to encircle a second anatomic part to provide for even compression of the soft tissue yet permitting full movement of the anatomic parts;
   first index means on said cincture means and said pendent means corresponding to said anatomic parts; and
   second index means on said cincture means, said pendent means and said tissue support wrap means.

2. The invention of claim 1 wherein said cincture means encircles a wearer's upper torso.

3. The invention of claim 1 wherein said cincture means encircles a wearer's waist.

4. The invention of claim 1 wherein said tissue support wrap means encircles a wearer's thigh.

5. The invention of claim 1 wherein said tissue support wrap means encircles a wearer's upper arm.

6. A soft tissue wound support garment comprising:
   cincture means configured to encircle a first anatomic part;
   pendent means suspended from said cincture means;
   tissue support wrap means suspended sidelong from said pendent means and configured to encircle a second anatomic part to provide for even compression of the soft tissue yet permitting full movement of the anatomic parts;
   first index means on said cincture means and said pendent means corresponding to said anatomic parts; and
   second index means on said cincture means, said pendent means and said tissue support means.

7. The invention of claim 6 wherein said first index means comprises symbols.

8. The invention of claim 6 wherein said second index means comprises color coding.

9. The invention of claim 6 wherein said second index means comprises symbols.

10. The invention of claim 6 wherein said second index means comprises color coding and symbols.

11. The invention of claim 6 wherein said cincture means encircles a wearer's waist.

12. The invention of claim 11 wherein said tissue support wrap means encircles a wearer's thigh.

13. The invention of claim 6 wherein said cincture means encircles a wearer's upper torso.

14. The invention of claim 13 wherein said tissue support wrap means encircles a wearer's upper arm.

15. A soft tissue wound support garment comprising:
   cincture means configured to encircle a first body part;
   pendent means suspended from said cincture means;
   tissue support wrap means suspended sidelong from said pendent means configured to encircle a second body part yet permitting full movement of the encircled body parts;
   closure means on said cincture means, said pendent means, and said tissue support wrap means, said closure means on said tissue support means corresponding to closure means on both said cincture means and said pendent means for positioning said garment on corresponding body parts for even compression of the soft tissue; and
   index means on said cincture means, said pendent means, and said tissue support wrap means.

16. The invention of claim 15 wherein said index means comprises color coding.

17. The invention of claim 15 wherein said index means comprises symbols.

18. The invention of claim 17 wherein said symbols comprise numbers.

19. The invention of claim 15 wherein said index means comprises color coding and symbols.

20. The invention of claim 19 wherein said symbols comprise numbers.

21. The invention of claim 15 wherein said cincture means encircles a wearer's waist.

22. The invention of claim 21 wherein said tissue support wrap means encircles a wearer's thigh.

23. The invention of claim 15 wherein said cincture means encircles a wearer's upper torso.

24. The invention of claim 23 wherein said tissue support wrap means encircles a wearer's upper arm.

25. The invention of claim 15 wherein said cincture means, said pendent means, and said tissue support wrap means all comprise elastic fabric.

26. The invention of claim 25 wherein said elastic fabric comprises one-ply elastic fabric.

27. The invention of claim 25 wherein said elastic fabric comprises two-ply elastic fabric.

28. The invention of claim 27 wherein said two-ply elastic fabric comprises two plies disposed in angularly overlapping relationship.

29. The invention of claim 28 wherein said two plies disposed in angularly overlapping relationship comprise two plies in orthogonally overlapping relationship.

* * * * *